US00PP35315P2

(12) United States Plant Patent
Moon

(10) Patent No.: US PP35,315 P2
(45) Date of Patent: Aug. 15, 2023

(54) ***QUERCUS* TREE NAMED 'QVMTFS'**

(50) Latin Name: *Quercus virginiana*
Varietal Denomination: QVMTFS

(71) Applicant: Dwayne Moon, Washington, GA (US)

(72) Inventor: Dwayne Moon, Washington, GA (US)

( * ) Notice: Subject to any disclaimer, the term of this patent is extended or adjusted under 35 U.S.C. 154(b) by 0 days.

(21) Appl. No.: 17/903,705

(22) Filed: Sep. 6, 2022

(51) Int. Cl.
*A01H 5/00* (2018.01)
*A01H 6/00* (2018.01)

(52) U.S. Cl.
USPC ..... Plt./225

(58) Field of Classification Search
USPC ..... Plt./225
CPC ..... A01H 5/04; A01H 5/00; A01H 6/00
See application file for complete search history.

(56) References Cited

U.S. PATENT DOCUMENTS

PP11,097 P * 10/1999 Sallin ..... Plt./225
PP17,249 P3 * 11/2006 Kelz ..... A01H 6/00 Plt./225
PP19,759 P2 * 2/2009 Easey ..... A01H 6/00 Plt./225

* cited by examiner

*Primary Examiner* — June Hwu
(74) *Attorney, Agent, or Firm* — Cassandra Bright

(57) ABSTRACT

A new and distinct cultivar of *Quercus virginiana* tree named 'QVMTFS' is disclosed, characterized by elongated shoots of growth and an open, oval-shaped canopy with a dominant central leader. Foliage is small, glossy and dark green. Resistance to gall has been observed. The new variety is a *Quercus* tree, typically used for landscapes and gardens.

3 Drawing Sheets

Latin name of the genus and species: *Quercus virginiana.*
Variety denomination: 'QVMTFS'.

BACKGROUND OF THE INVENTION

The new cultivar is a product of a planned breeding program. The new variety was discovered growing as a seedling among a group of open-pollinated *Quercus virginiana* trees at a tree farm in Washington, Ga. A single seedling tree was observed which had unique rapid new shoot growth not observed in the other seedlings among this group. The inventor made this discovery in 2015. The exact seed and pollen parents cannot be identified.

Asexual reproduction by grafting of the new cultivar 'QVMTFS' was first performed in 2017 at a farm in Washington, Ga. The cleft grafting system developed by the inventor has resulted in progeny that have proven the characteristics of the new variety to be genetically stable. This grafting process involved taking cuttings in February, being grafted, and being placed in calloused chambers for approximately three weeks. They are then moved into 3"×6" tree band pots and placed in humidity chambers for approximately four weeks. Furthermore, these observations have confirmed that the new variety represents a new and improved variety of *Quercus virginiana* tree as particularly evidenced by the smaller leaf, darker more dense willow oak, holds foliage longer, dark green mature growth against bright new growth, and dominant central leader. These genetic traits can be consistently reproduced by asexual propagation.

SUMMARY OF THE INVENTION

The cultivar 'QVMTFS' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'QVMTFS' grown in Washington, Ga. These characteristics in combination distinguish 'QVMTFS' as a new and distinct *Quercus virginiana* cultivar:

1. Elongated shoots of growth. Unique growth spurts of 10 to 15 cm occur 4 to 6 times per year, resulting in 30 to 40 cm of new growth per year. Typically *Quercus virginiana* has a single growth spurt per year.
2. Full headed; oval shape.
3. Loose open structure.
4. Dominant central leader.
5. Resistance to gall.
6. Dark, glossy small leaf.

PARENT COMPARISON

The exact parent varieties cannot be identified.

COMMERCIAL COMPARISON

Plants of the new cultivar 'QVMTFS' are similar to plants of *Quercus virginiana* 'FBQV22', U.S. Plant Pat. No. 19,758, in most horticultural characteristics, however, plants of the new cultivar 'QVMTFS' differ in the following:

1. The new variety has an oval shape; this comparator has a pyramidal habit.
2. The new variety produces elongated shoots of growth not found in this comparator.
3. The new variety has been observed resistant to gall; this comparator has been observed susceptible.

Plants of the new cultivar 'QVMTFS' are similar to plants of *Quercus virginiana* 'Cannon-Sharp', U.S. Plant Pat. No.

19,608, in most horticultural characteristics, however, plants of the new cultivar 'QVMTFS' differ in the following:

1. Foliage of the new variety is somewhat larger than foliage of this comparator.
2. The new variety produces elongated shoots of growth not found in this comparator.
3. Canopy of the new variety is not as dense as the canopy of this comparator.

Plants of the new cultivar 'QVMTFS' are similar to plants of *Quercus virginiana* 'SDLN', U.S. Plant Pat. No. 12,015, in most horticultural characteristics, however, plants of the new cultivar 'QVMTFS' differ in the following:

1. The new variety produces elongated shoots of growth not found in this comparator.
2. Canopy of the new variety is not as dense as the canopy of this comparator.

Plants of the new cultivar 'QVMTFS' are similar to plants of *Quercus virginiana* 'Grandview Gold', unpatented, in most horticultural characteristics, however, plants of the new cultivar 'QVMTFS' differ in the following:

1. The new variety has dark green foliage; foliage of this comparator is golden.

Plants of the new cultivar 'QVMTFS' are similar to plants of *Quercus virginiana* 'QVTIA', U.S. Plant Pat. No. 11,219, in most horticultural characteristics, however, plants of the new cultivar 'QVMTFS' differ in the following:

1. The new variety has an oval shape; this comparator has a pyramidal habit.
2. The new variety produces elongated shoots of growth not found in this comparator.

Plants of the new cultivar 'QVMTFS' are similar to plants of *Quercus virginiana* 'K-1', U.S. Plant Pat. No. 17,249, in most horticultural characteristics, however, plants of the new cultivar 'QVMTFS' differ in the following:

1. The new variety has an oval shape; this comparator has a columnar habit.
2. Canopy of the new variety is not as dense as the canopy of this comparator.

Plants of the new cultivar 'QVMTFS' are similar to plants of *Quercus virginiana* 'CLTF21', U.S. Plant Pat. No. 11,097, in most horticultural characteristics, however, plants of the new cultivar 'QVMTFS' differ in the following:

1. Canopy of the new variety is not as dense as the canopy of this comparator.
2. Foliage of the new variety is smaller than foliage of this comparator.

Plants of the new cultivar 'QVMTFS' are similar to plants of *Quercus virginiana* 'FBQV1', U.S. Plant Pat. No. 19,759, in most horticultural characteristics, however, plants of the new cultivar 'QVMTFS' differ in the following:

1. 'QVMTFS' is a more upright, narrow tree. A 6-inch caliper tree of 'QVMTFS' typically has a height of 20 feet and a width of 6. 'FBQV1' forms smaller branches developing off secondary branches forming a broad canopy at early age.

BRIEF DESCRIPTION OF THE PHOTOGRAPHS

The accompanying photograph in FIG. 1 illustrates a typical tree of the new variety at about 4 years of age.

Figure 1:
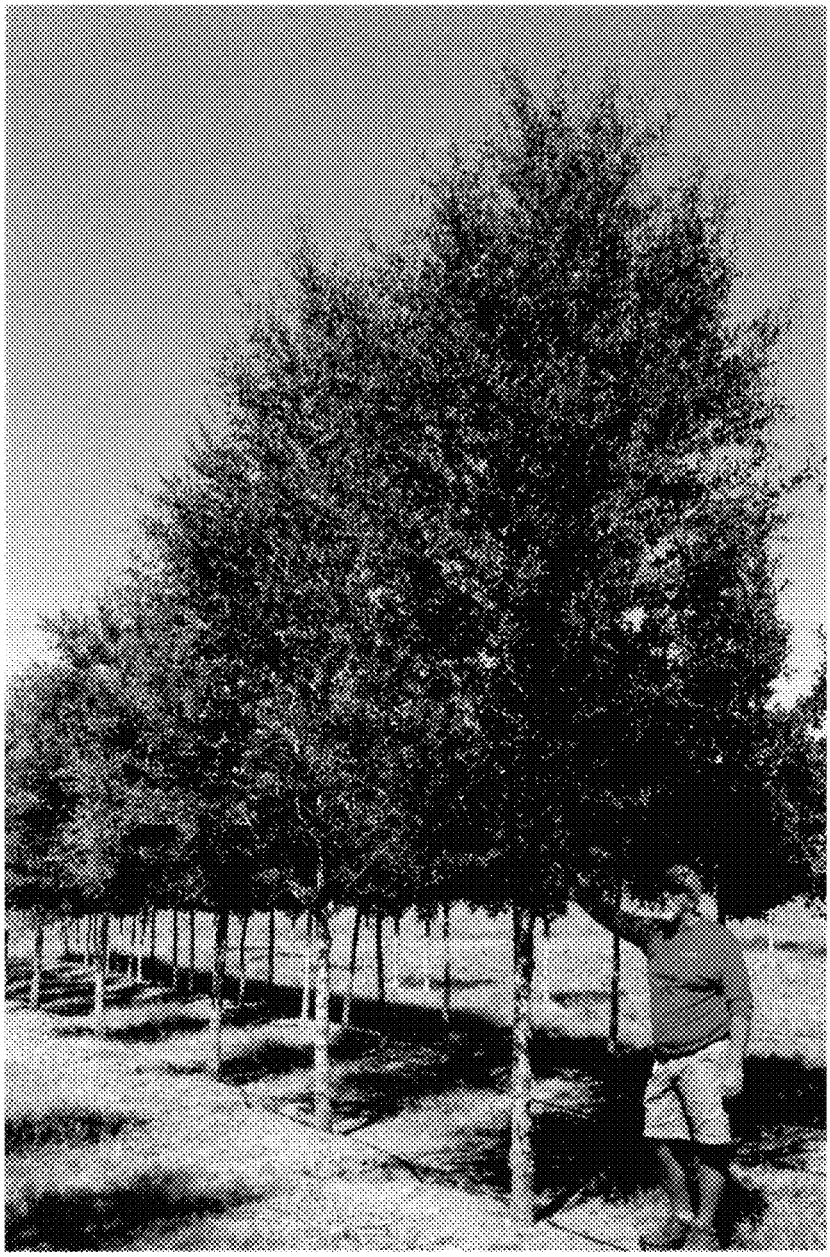
Figure 2:
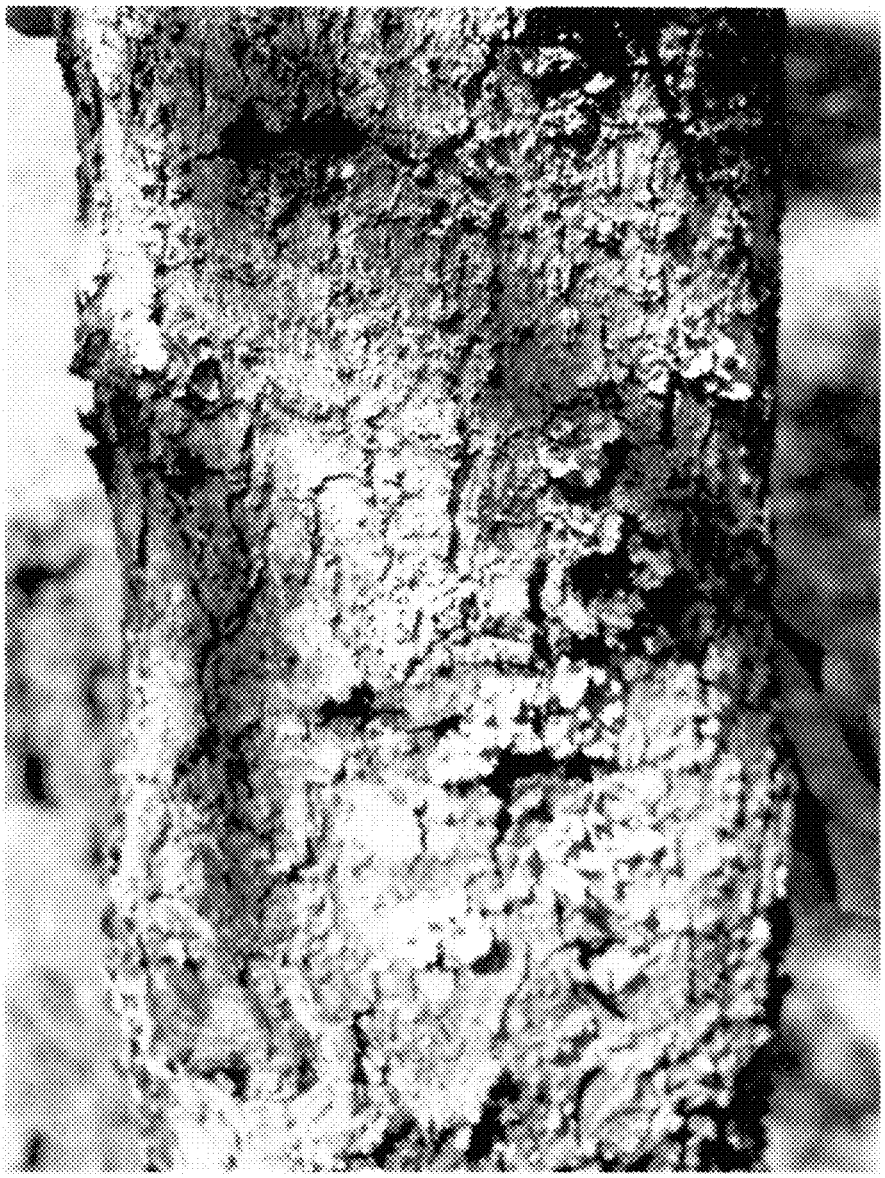
FIG. 2 illustrates a close-up view of the trunk.
Figure 3:
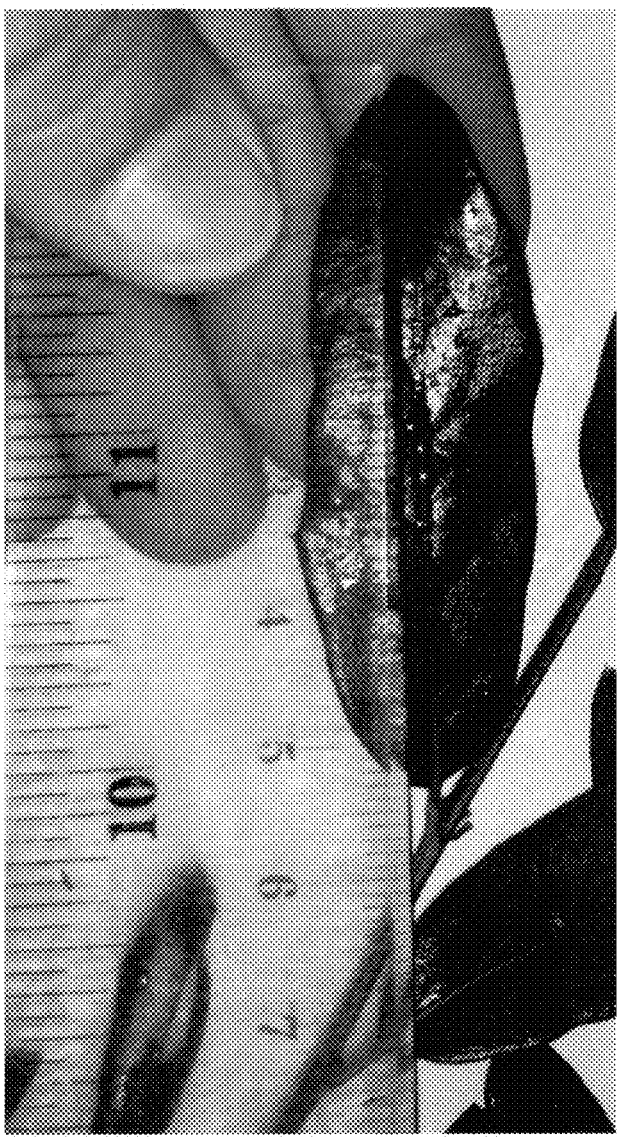
FIG. 3 illustrates typical foliage of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'QVMTFS' plants grown outdoors and in a nursery in Washington, Ga. Plants are approximately 2 years old, in a 3 gallon nursery container. Temperatures ranged from 5° C. to 10° C. at night to 18° C. to 27° C. during the day. Measurements and numerical values represent averages of typical plant types.

Botanical classification: *Quercus virginiana* 'QVMTFS'.

PROPAGATION

Cleft grafting.

Root description: Woody. Brown roots not accurately measured with an R.H.S. Colour Chart.

TREE

Growth habit: Evergreen tree with an open, oval-shaped canopy.

Height: Approximately 21 feet at 5 years.

Spread: Approximately 6 feet at 5 years.

Branch aspect and angle: Lower branches at obtuse angles, upper branches 45 degrees or less.

Branch/stem color:

*New growth*.—Near RHS Greyed-Green 195A.

*Mature*.—Near RHS Greyed-Green 197D, speckles or streaks near Grey-Grown N199C.

Growth rate: Rapid.

Trunk characteristics:

*Diameter*.—About 4.5 inches measured at approximately 3 inches above soil level at 3 years.

*Color*.—Near RHS Greyed-Brown N199D and Greyed-Green 197A. Bark Black 202C 202D and Greyed-Green 197B, 197C and 197D.

*Surface texture*.—Moderately scaled bark.

FOLIAGE

Leaf:

*Arrangement*.—Alternate.

*Shape*.—Ovate.

*Average length*.—Approximately 4.5 to 5.5 cm excluding petiole.

*Average width*.—Approximately 1.5 cm.

*Apex*.—Broad acute.

*Base*.—Broad taper.

*Margin*.—Entire. Irregular pointed protrusions occasionally present.

*Texture of top surface*.—Glabrous.

*Texture of lower surface*.—Very minute trichomes, less than 1 mm, colored near Yellow-Green 145D.

*Color*.—Young foliage: Upper side: Near RHS Yellow-Green 144A. Under side: Near RHS Yellow-Green 144B. Mature foliage: Upper side: Near RHS Green 139A. Under side: Near RHS Green 138A. Fall foliage: No color change in the Fall.

*Venation*.—Type: Pinnate. Color: Venation color upper side: Near RHS Yellow-Green N144B. Venation color under side: Near RHS Yellow-Green 145A.

*Petiole*.—Length: Average 8 mm. Diameter: Average 2 mm. Color: Upper side: Near RHS Yellow-Green N144A. Under side: Near RHS Yellow-Green 144C.

FLOWER

Not observed.

REPRODUCTIVE ORGANS

Not observed.

OTHER CHARACTERISTICS

Disease/pest resistance: Breeder has observed resistance to Oak gall. Neither resistance nor susceptibility to other normal diseases and pests of *Quercus* has been observed.

Drought tolerance: No tolerance for drought observed.

Temperature tolerance: USDA Zones 8 through 10.

Fruits/nuts: Not observed.

What is claimed is:

1. A new and distinct cultivar of *Quercus virginiana* tree named 'QVMTFS' as herein illustrated and described.

* * * * *